(12) United States Patent
Mohr et al.

(10) Patent No.: US 6,968,032 B2
(45) Date of Patent: Nov. 22, 2005

(54) SYSTEMS AND METHODS FOR FILTERING IMAGES

(75) Inventors: Kelly Ann Mohr, New Berlin, WI (US); Darin R. Okerlund, Muskego, WI (US); Laurent Launay, Saint Remy les Chevreuse (FR); Helen Jane Thomson, Milwaukee, WI (US)

(73) Assignee: GE Medical Systems Global Technologies Company, LLC, Waukesha, WI (US)

( * ) Notice: Subject to any disclaimer, the term of this patent is extended or adjusted under 35 U.S.C. 154(b) by 117 days.

(21) Appl. No.: 10/739,619

(22) Filed: Dec. 18, 2003

(65) Prior Publication Data

US 2005/0135554 A1    Jun. 23, 2005

(51) Int. Cl.[7] .................................. A61B 6/03
(52) U.S. Cl. .................. 378/8; 378/4; 378/901
(58) Field of Search ............... 378/4, 8, 15, 901; 382/131, 260, 261; 250/370.09

(56) References Cited

U.S. PATENT DOCUMENTS

| | | |
|---|---|---|
| 4,047,041 A | 9/1977 | Houston |
| 4,055,767 A | 10/1977 | Allemand |
| 4,705,049 A | 11/1987 | John |
| 4,991,092 A | 2/1991 | Greensite |
| 5,131,021 A | 7/1992 | Gard et al. |
| 5,799,057 A | 8/1998 | Hoffman et al. |
| 6,501,975 B2 | 12/2002 | Diab et al. |
| 6,526,117 B1 | 2/2003 | Okerlund et al. |

*Primary Examiner*—David V Bruce
(74) *Attorney, Agent, or Firm*—Carl B. Horton, Esq.; Armstrong Teasdale LLP

(57) ABSTRACT

A method for filtering images is provided. The method includes obtaining at least one set of image data of a subject using an imaging system, removing at least one slice of image data from the at least one set to form a filtered set, and reconstructing images from the filtered set.

25 Claims, 7 Drawing Sheets

SYSTEMS AND METHODS FOR FILTERING IMAGES

BACKGROUND OF THE INVENTION

This invention relates generally to post-processing of images and particularly to systems and methods for filtering images.

Millimeter and sub-millimeter slices are achievable in multidetector computed tomography (MDCT) scanners. These slices are beneficial for providing great z-resolution within a set of images. Despite the improvement in z-resolution within the set of images, banding artifacts can be quite apparent in ventricle walls when viewing the set of images from a sagittal or a coronal perspective. Another artifact that can be seen in cardiac exams is a misregistration artifact resulting from acquisition with a helical pitch that is too fast for a given heart rate.

BRIEF DESCRIPTION OF THE INVENTION

In one aspect, a method for filtering images is provided. The method includes obtaining at least one set of image data of a subject using an imaging system, removing at least one slice of image data from the at least one set to form a filtered set, and reconstructing images from the filtered set.

In another aspect, a method for filtering images is provided. The method includes obtaining at least one set of image data over a range of z-locations after scanning a subject, wherein each set is acquired at the same time in a physiological cycle of motion of an object within the subject, and removing at least one slice of image data from the at least one set.

In yet another aspect, a computer-readable medium encoded with a program is provided. The program is configured to obtain at least one set of image data of a subject using an imaging system, remove at least one slice of image data from the at least one set to form a filtered set, and reconstruct images from the filtered set.

In still another aspect, a computed tomography (CT) system is provided. The CT system includes an X-ray source configured to generate X-rays, a detector configured to detect the X-rays to generate electrical signals, a data acquisition system (DAS) for sampling the electrical signals to create projection data that is converted into at least one set of image data, and a controller. The controller is configured to obtain the at least one set of image data of a subject using the CT system, remove at least one slice of image data from the at least one set to form a filtered set, and reconstruct images from the filtered set.

In another aspect, a computer is provided. The computer is configured to obtain at least one set of image data of a subject using an imaging system, remove at least one slice of image data from the at least one set to form a filtered set, and reconstruct images from the filtered set.

DETAILED DESCRIPTION OF THE INVENTION

Figure 1:
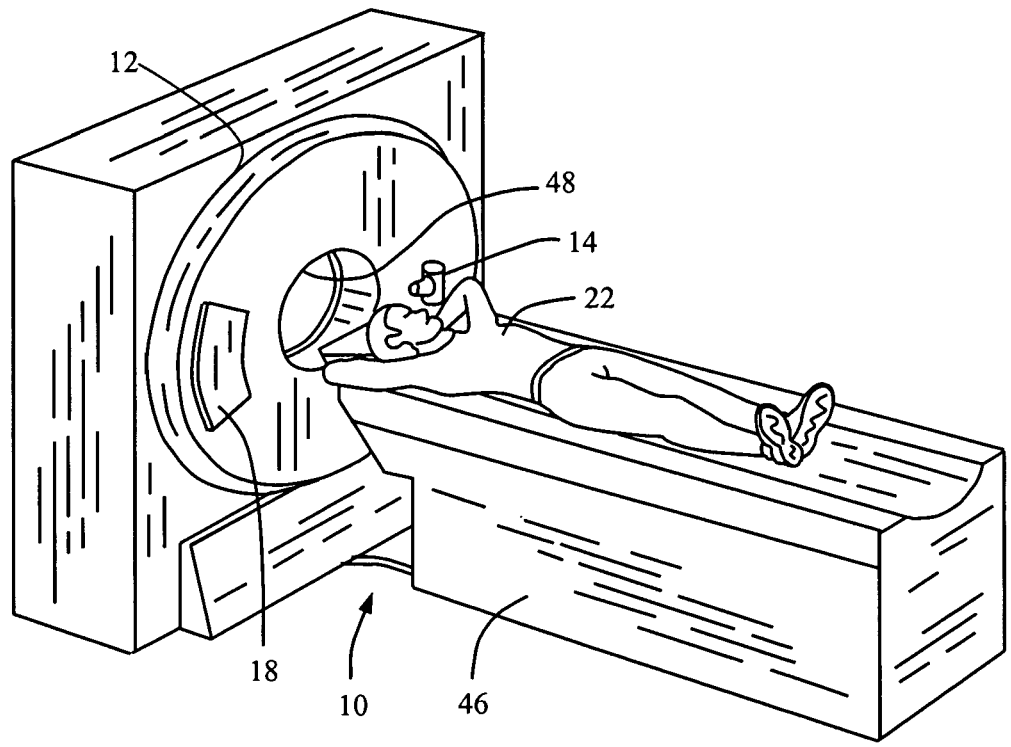
FIG. 1 is a perspective view of a computed tomography (CT) imaging system in which systems and methods for filtering images are implemented.

In computed tomography (CT) imaging system configurations, an X-ray source projects a fan-shaped beam which is collimated to lie within an X-Y plane of a Cartesian coordinate system and generally referred to as an "imaging plane". The X-ray beam passes through a subject, such as a patient, being imaged. The beam, after being attenuated by the subject, impinges upon an array of radiation detectors. The intensity of the attenuated radiation beam received at the detector array is dependent upon the attenuation of an X-ray beam by the subject. Each detector element of the array produces a separate electrical signal that is a measurement of the beam intensity at the detector location. The intensity measurements from all of the detectors are acquired separately to produce a transmission profile.

In third generation CT systems, the X-ray source and the detector array are rotated with a gantry within the imaging plane and around the subject to be imaged such that the angle at which the X-ray beam intersects the subject constantly changes. A group of X-ray attenuation measurements, i.e., projection data, from the detector array at one gantry angle is referred to as a "view". A "scan" of the subject comprises a set of views made at different gantry angles, or view angles, during one revolution of the X-ray source and detector. Examples of a scan include an axial scan, a cine scan, and a helical scan.

In an axial scan, the projection data is processed to construct an image that corresponds to a 2-dimensional (2D) slice taken through the subject. One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a cathode ray tube display.

To reduce the total scan time, a "helical" scan may be performed. To perform a "helical" scan, the patient is moved while the data for the prescribed number of slices is acquired. Such a system generates a single helix from a fan beam helical scan. The helix mapped out by the fan beam yields projection data from which images in each prescribed slice may be reconstructed.

Reconstruction algorithms for helical scanning typically use helical weighting algorithms that weight the collected data as a function of view angle and detector channel index. Specifically, prior to a filtered back projection process, the data is weighted according to a helical weighting factor, which is a function of both the gantry angle and detector angle. The weighted data is then processed to generate CT numbers and to construct an image that corresponds to a two dimensional slice taken through the subject.

As used herein, an element or step recited in the singular and preceded with the word "a" or "an" should be understood as not excluding plural the elements or steps, unless such exclusion is explicitly recited. Furthermore, references to "one embodiment" of the present invention are not intended to be interpreted as excluding the existence of additional embodiments that also incorporate the recited features.

Also as used herein, the phrase "reconstructing an image" is not intended to exclude embodiments of the present invention in which data representing an image is generated but a viewable image is not. Therefore, as used herein the term "image" broadly refers to both viewable mages and data representing a viewable image. However, many embodiments generate (or are configured to generate) at least one viewable image.

Figure 2:
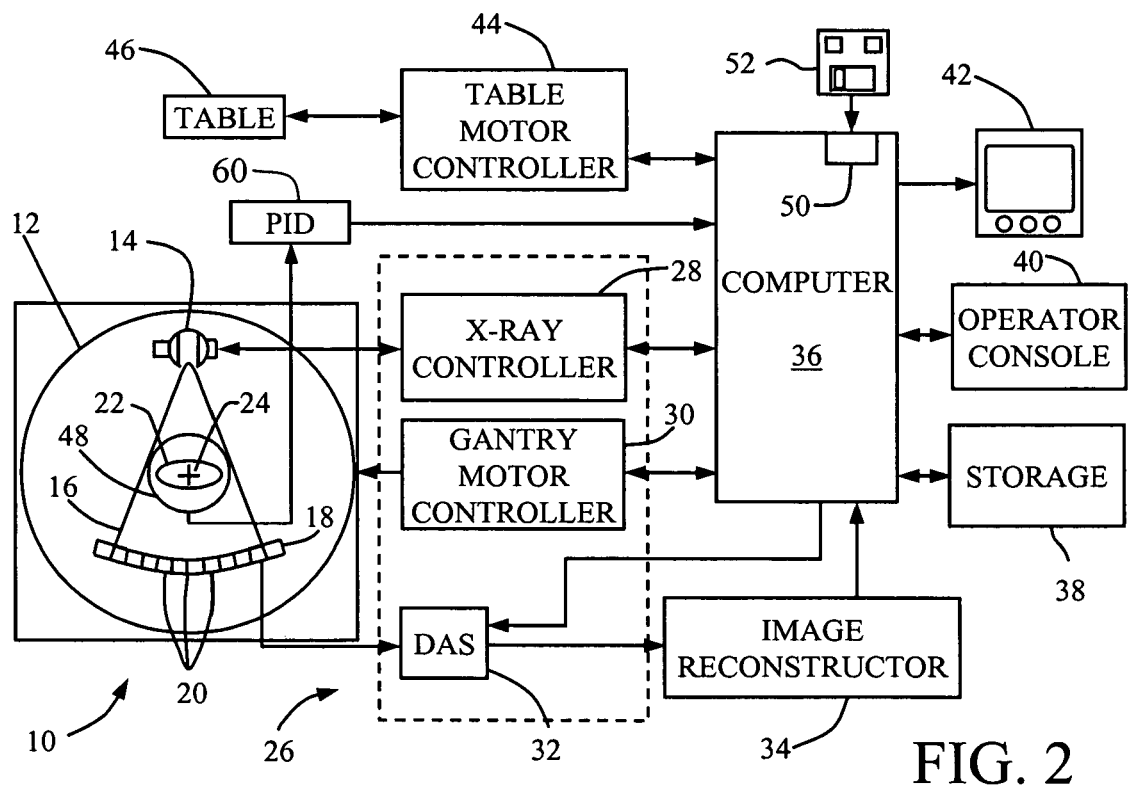
FIG. 2 is a block diagram of the CT system of FIG. 1.

Referring to FIGS. 1 and 2, a multi-slice scanning imaging system, for example, a CT imaging system 10, is shown as including a gantry 12 representative of a "third generation" CT imaging system. Gantry 12 has an X-ray source 14 that projects a beam of X-rays 16 toward a detector array 18 on the opposite side of gantry 12. Detector array 18 is formed by a plurality of detector rows (not shown) including a plurality of detector elements 20 which together sense the projected X-rays that pass through a subject, such as a medical patient 22. Each detector element 20 produces an electrical signal that represents the intensity of an impinging X-ray beam and hence allows estimation of the attenuation of the beam as it passes through patient 22. During a scan to acquire X-ray projection data, gantry 12 and the components mounted thereon rotate about a center of rotation 24. After data acquisition, the data is stored as helical data in a mass storage device 38 and can be weighted and filtered to generate slice image data corresponding to separate transaxial slice images.

FIG. 2 shows only a detector row of detector elements 20. However, multislice detector array 18 includes a plurality of parallel detector rows of detector elements 20 such that projection data corresponding to a plurality of quasi-parallel or parallel slices can be acquired simultaneously during a scan.

Rotation of gantry 12 and the operation of X-ray source 14 are governed by a control mechanism 26 of CT system 10. Control mechanism 26 includes an X-ray controller 28 that provides power and timing signals to X-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized X-ray data from DAS 32 and performs high-speed image reconstruction. The reconstructed image is applied as an input to a computer 36 which stores the image in mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, X-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

Computer 36 is electrically coupled to a physiological information device (PID) 60 to identify or determine, a physiological cycle of an object, such as, heart or lungs, of patient 22. More specifically, PID 60 is coupled to computer 36 and generates a physiological cycle signal representative of cardiac contractions or respiration, including a plurality of phases, of patient 22.

In one embodiment, computer 36 includes a device 50, for example, a floppy disk drive or CD-ROM drive, for reading instructions and/or data from computer-readable medium 52, such as a floppy disk, a compact disc-read only memory (CD-ROM), a magneto-optical disk (MOD), or a digital versatile disc (DVD). In another embodiment, computer 36 executes instructions stored in firmware (not shown). Computer 36 is programmed to perform functions described herein, and as used herein, the term computer is not limited to just those integrated circuits referred to in the art as computers, but broadly refers to computers, processors, microcontrollers, microcomputers, programmable logic controllers, application specific integrated circuits, and other programmable circuits, and these terms are used interchangeably herein.

Although the specific embodiment mentioned above refers to a third generation CT system, methods for filtering images equally apply to fourth generation CT systems that have a stationary detector and a rotating X-ray source, fifth generation CT systems that have a stationary detector and an X-ray source.

Additionally, although the herein described methods are described in a medical setting, it is contemplated that the benefits of the methods accrue to non-medical imaging systems such as those systems typically employed in an industrial setting or a transportation setting, such as, for example, but not limited to, a baggage scanning system for an airport, other transportation centers, government buildings, office buildings, and the like. The benefits also accrue to micro PET and CT systems which are sized to study lab animals as opposed to humans.

Figure 3:
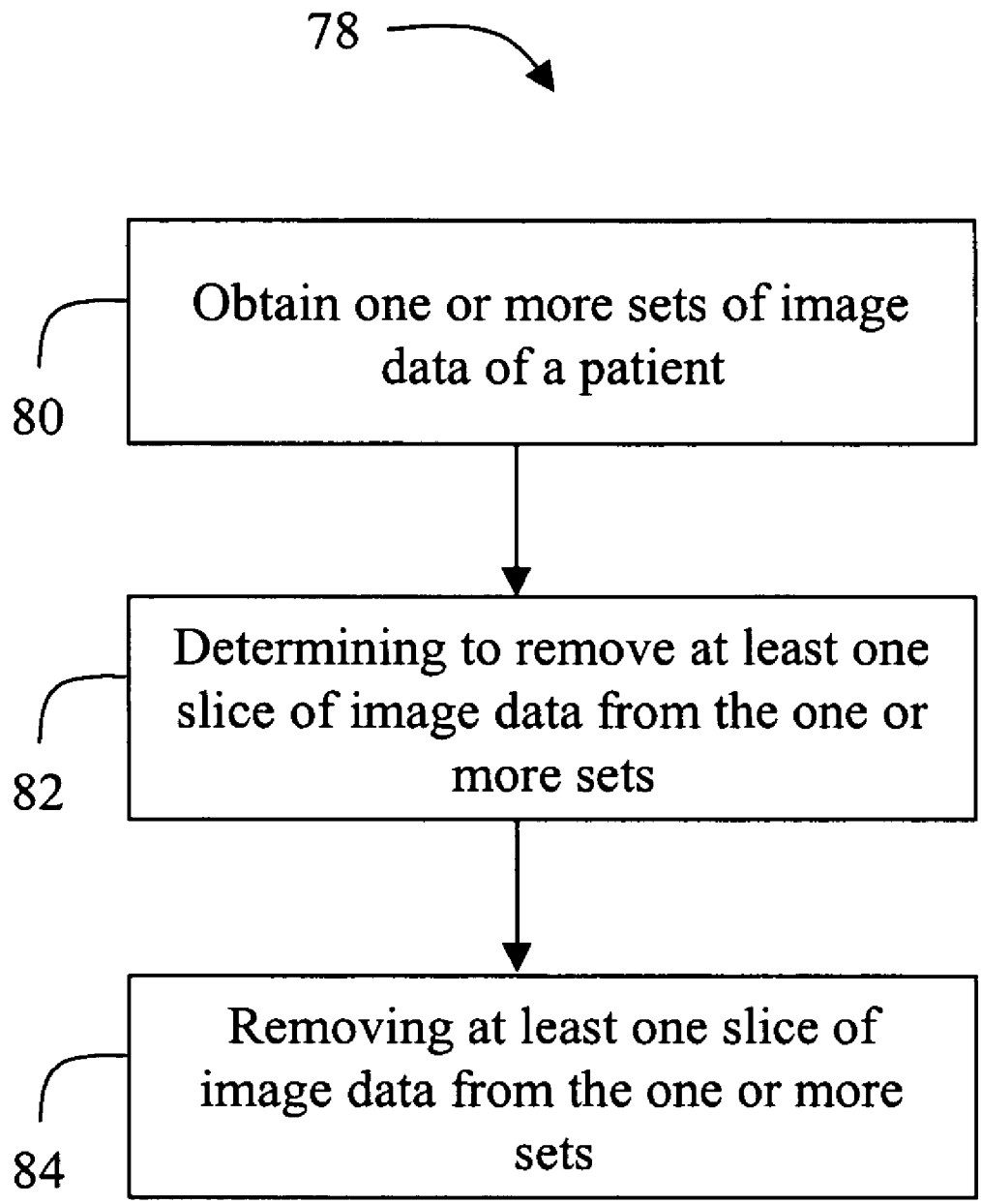
FIG. 3 illustrates a method for filtering images.

FIG. 3 illustrates a method 78 for filtering images. Method 78 is stored in mass storage device 38 or in computer-readable medium 52. Method 78 is executed by computer 36. Method 78 includes obtaining 80 one or more sets of image data of patient 22. The image data is obtained by using CT system 10. Method 78 further includes determining 82 to remove at least one slice of image data from the one or more sets of image data. Method 78 also includes removing 84 at least one slice of image data from the one or more sets to form a filtered set of image data. 2-dimensional or 3-dimensional (3D) images can be re-constructed from the filtered set by image reconstructor 34.

Figure 4:
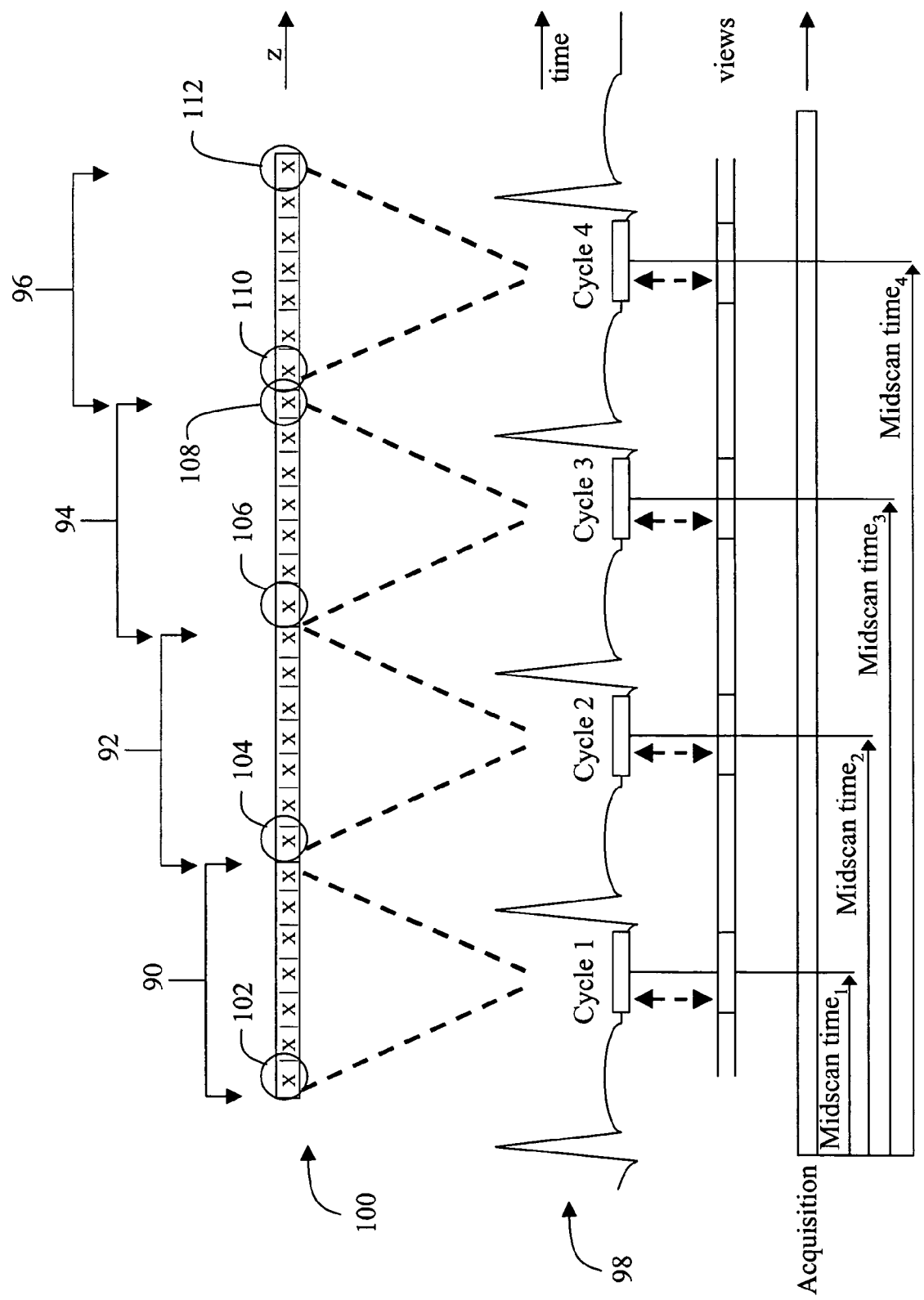
FIGS. 4 and 5 illustrate an embodiment of the method of FIG. 3.
Figure 5:
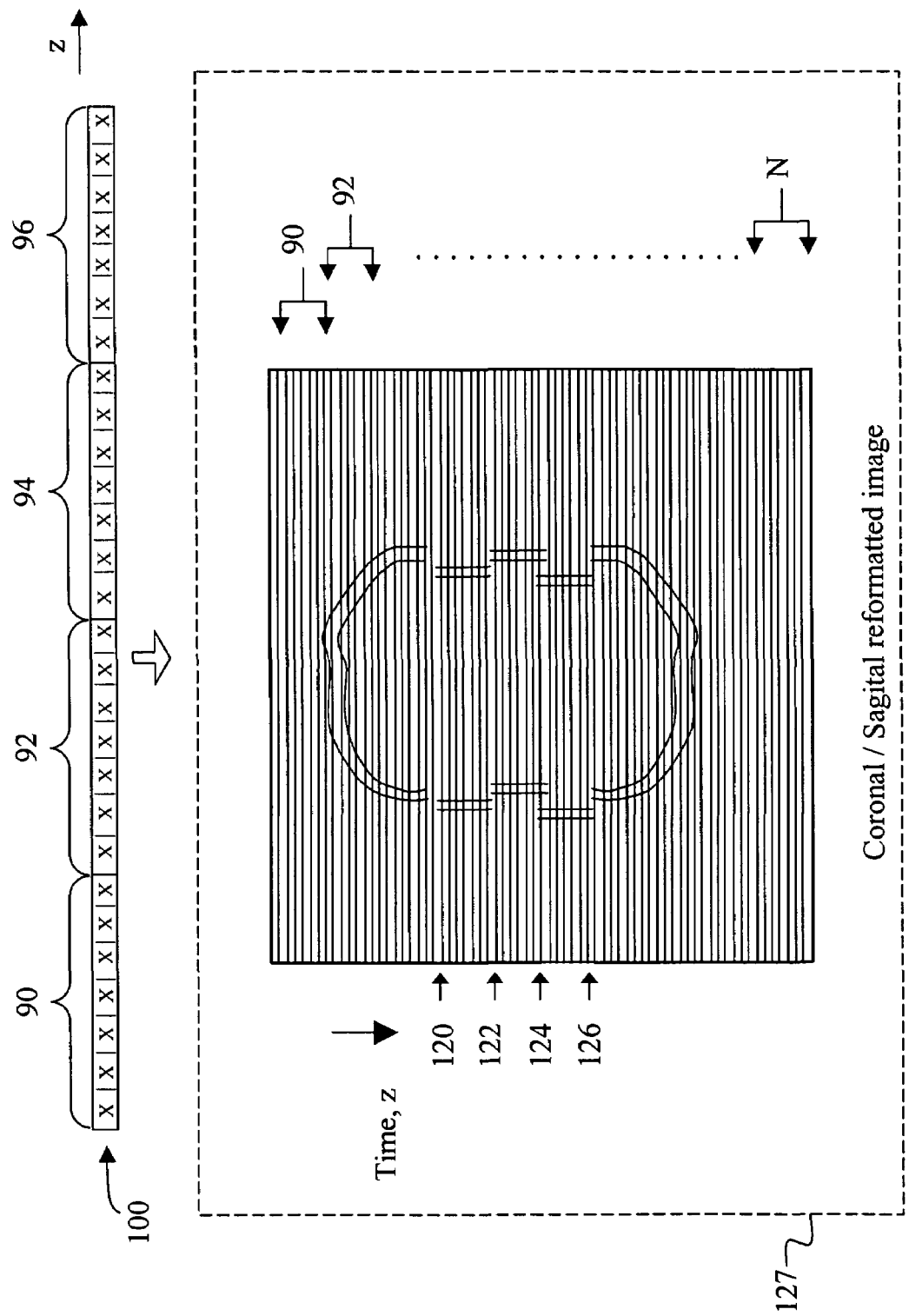

FIGS. 4 and 5 illustrate an embodiment of method 78 for filtering images. A plurality of sets 90, 92, 94, and 96 of image data are obtained by weighting and filtering projection data acquired by scanning patient 22. A higher or a lower number N of sets 90, 92, 94, and 96 than four can be obtained. Each set 90, 92, 94, or 96 of image data has seven slices of image data. A higher or a lower number of slices of image data than seven slices can be obtained. Sets 90, 92, 94, and 96 may not have an equal number of slices. For instance, set 90 has eight slices and set 92 has nine slices. Each set 90, 92, 94, or 96 is acquired at the same time, such as during a diastolic phase, in a physiological cycle of a physiological cycle signal 98 representing motion of an object, such as a heart, of patient 22. The sets 90, 92, 94, and 96 are obtained along a range of z-locations on a z-axis that lies along a length of patient 22. For instance, set 90 is obtained along a range $z_1$–$z_2$, set 92 is obtained along a range $z_2$–$z_3$, set 94 is obtained along a range $z_3$–$z_4$, and set 96 is obtained along a range $z_4$–$z_5$. Sets 90, 92, 94, and 96 that are consecutively ordered along the z-axis are referred to as an array 100.

Computer 36 obtains image sets 90, 92, 94, and 96, and filters a slice, such as a slice 102 or a slice 104, of image data in at least one of sets 90, 92, 94, and 96. A slice that has the lowest z-location of all z-locations in a set of image data that includes the slice, is referred to as a first slice. The first slice may be filtered by using method 78 for filtering images. For example, slice 102 of image data is a first slice in set 90 since it has the lowest z-location of all z-locations in set 90. As another example, slice 104 of image data is a first slice in set 92 since it has the lowest z-location of all z-locations in set 92.

In an alternative embodiment, computer 36 filters a first slice and a last slice of image data from at least one set of image data. For example, computer 36 filters slices 106 and 108 of image data from set 94 and filters slices 110 and 112 of image data from set 96. A last slice that is filtered in a set is located at the highest z-location of all z-locations in the set. For example, slice 108 is a last slice in set 94. As another example, slice 112 is a last slice in set 96.

In another alternative embodiment, computer 36 filters a first slice from some sets of image data and filters a first slice and a last slice from some other sets of image data. For example, computer 36 filters slice 102 from set 90, and filters slices 106 and 108 from set 96.

In yet another alternative embodiment, computer 36 filters a last slice from some sets of image data and filters a first slice and a last slice from some other sets of image data. For example, computer 36 filters slice 108 from set 94, and filters slices 110 and 112 from set 96. A filter, such as a comb filter, is used to filter one or more slices of image data from a set of image data.

In still another alternative embodiment, computer 36 filters a last slice of image data from at least one set of image data. For example, computer 36 filters slice 108 of image data from set 94 and filters slice 112 of image data from set 96.

To filter one or more slices of image data in sets 90, 92, 94, or 96, computer 36 identifies changes in midscan times within array 100. All slices of image data within a set of image data have the same midscan time and so a change in midscan time indicates an end of a set of image data and a beginning of a consecutive set of image data. Midscan time of a set of image data is a period of time from the beginning of an exam of patient 22 to a time at which the set is acquired. All slices of image data within set 90 have the same $\text{midscan time}_1$, all slices of image data within set 92 have the same $\text{midscan time}_2$, all slices of image data within set 94 have the same $\text{midscan time}_3$, and all slices of image data within set 96 have the same $\text{midscan time}_4$. So, there is a change in midscan time between a last slice of set 90 and slice 104 of set 92, a change in midscan between a last slice of set 92 and slice 106 of set 94, and a change in midscan between slice 108 of set 94 and slice 110 of set 96.

Once computer 36 identifies a change in a midscan time within array 100, computer 36 also identifies a first slice and a last slice in each set 90, 92, 94, or 96 to perform filtering of the first and/or the last slice. To smooth gaps formed by filtering in sets 90, 92, 94, and 96, a linear, cubic, or a higher order interpolation is applied to sets 90, 92, 94, and 96. Examples of higher order interpolation include any interpolation greater than a second order interpolation.

Filtering removes banding artifacts at edges of one or more of sets 90, 92, 94, and 96. Banding artifacts at edges 120, 122, 124, and 126 of one or more sets are shown in FIG. 5, which includes a coronal/sagital reformatted image 127. Banding is a shift in gray scale intensity between two consecutive sets of sets 90, 92, 94, and 96. Banding can be caused by a change in contrast intensity over time and by beam hardening. Banding artifacts are quite apparent in ventricle walls of patient 22 when viewing images with a multiplanar reformat rendering from a sagittal or a coronal perspective. Banding can be apparent in a right atrium of patient 22, where contrast mixing may cause significant intensity shifts from one physiological cycle to another physiological cycle. Moreover, banding artifacts can be apparent in coronary arteries of patient 22 when viewing images with a curved reformat rendering. Filtering that is described above eliminates banding artifacts caused by supersampling and by thin slices, such as slices 104, 106, 108, 110, and 112, of image data at edges 120, 122, 124, and 126.

Figure 6:
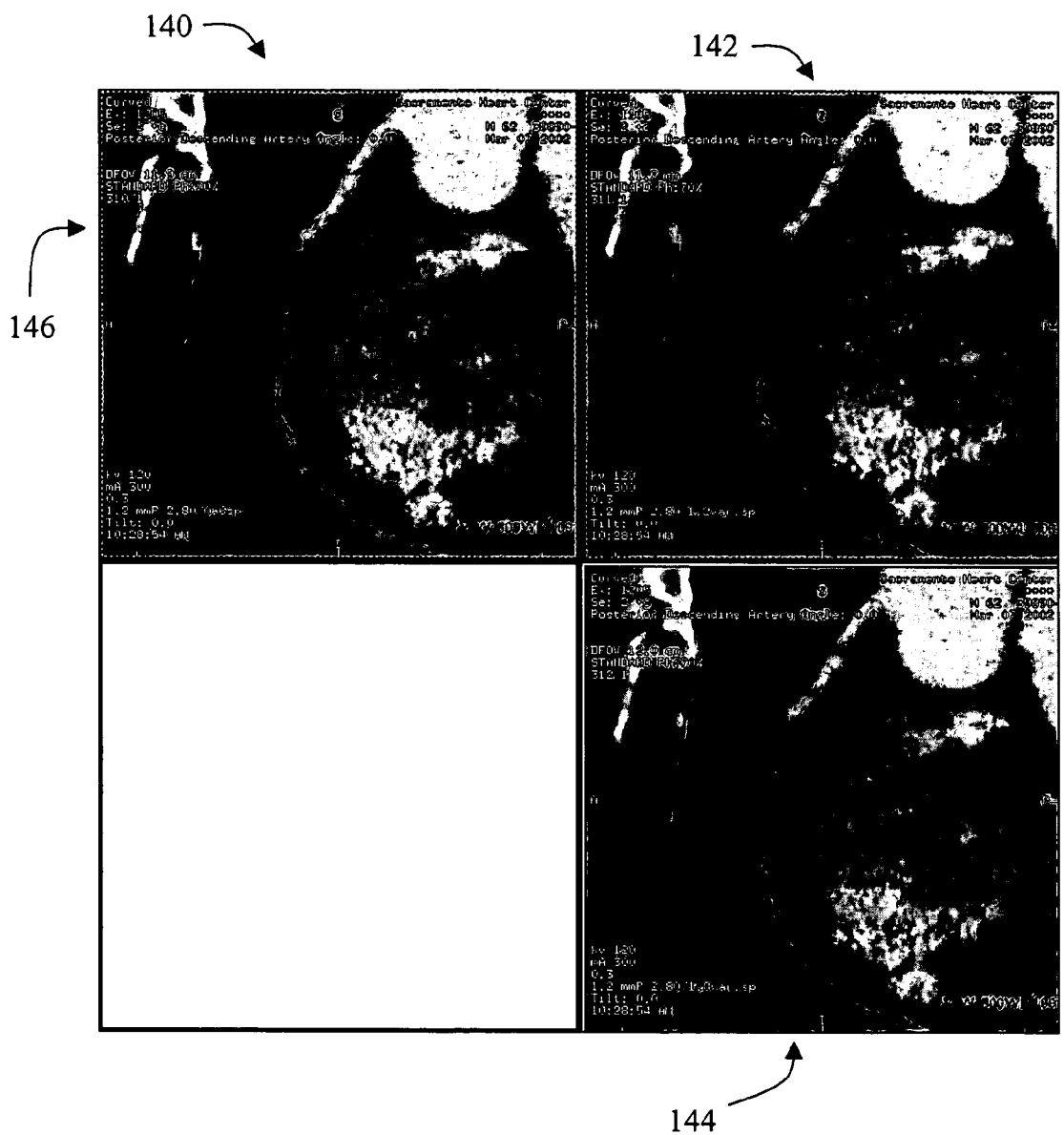
FIG. 6 shows images displaying effects of implementing the method of FIGS. 4 and 5.

FIG. 6 shows images 140, 142, and 144 of a right coronary artery of patient 22. Images 140, 142, and 144 are obtained by curved reformatting. Image 140 is an image that is obtained without executing method 78 for filtering images and banding artifacts are visible in image 140. Image 142 is an image obtained by removing a last slice of image data from a set 146 of image data. Image 144 is an image obtained by removing a first slice and a last slice of image data in set 146. Banding is significantly reduced in image 144.

Figure 7:
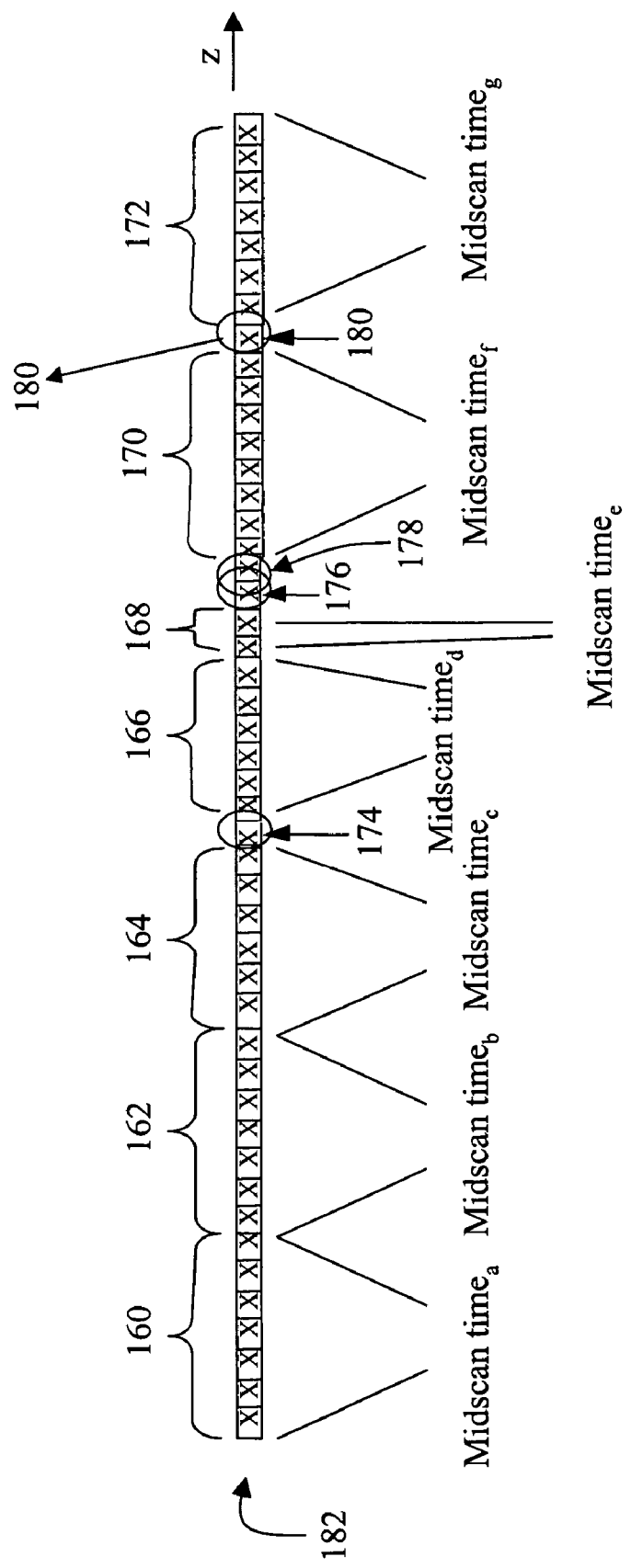
FIGS. 7 and 8 illustrate another embodiment of the method of FIG. 3.
Figure 8:
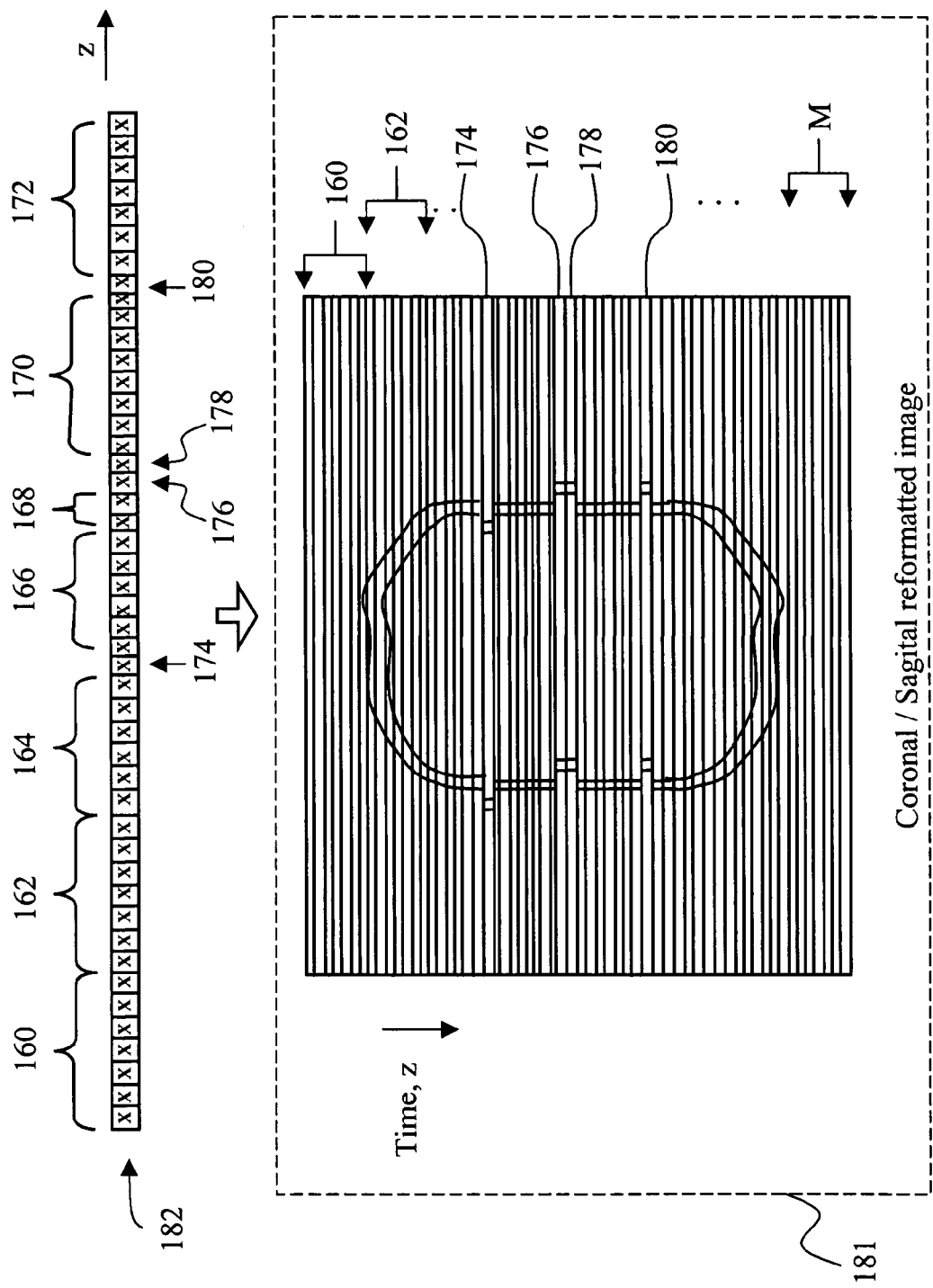

FIGS. 7 and 8 illustrate another embodiment of method 78 for filtering images. Sets 160, 162, 164, 166, 168, 170, and 172 of image data and slices 174, 176, 178, and 180 of ungated image data are obtained by weighting and filtering projection data acquired by scanning patient 22. A higher or a lower number of slices of ungated image data than four can be obtained. Moreover, a higher or a lower number M of sets than seven sets can be obtained. Each set 160, 162, 164, 166, 168, 170, or 172 of image data has seven slices of image data. Alternatively, each set 160, 162, 164, 166, 168, 170, or 172 of image data has two or more slices of image data. Sets 160, 162, 164, 166, 168, 170, and 172 may not have the same number of slices. For example, set 160 has six slices of image data and set 172 has nine slices of image data. Each set 160, 162, 164, 166, 168, 170, or 172 is acquired at the same time, such as during a diastolic phase, in a physiological cycle of a physiological cycle signal representing motion of the object of patient 22. Sets 160, 162, 164, 166, 168, 170, and 172 are obtained along a range of z-locations on the z-axis. For example, set 160 is obtained along a range $z_1$–$z_2$, set 162 is obtained along a range $z_2$–$z_3$, set 164 is obtained along a range $z_3$–$z_4$, set 166 is obtained along a range $z_5$–$z_6$, set 168 is obtained along a range $z_6$–$z_7$, set 170 is obtained along a range $z_8$–$z_9$, and set 172 is obtained along a range $z_{10}$–$z_{11}$. Each slice 174, 176, 178, or 180 of ungated image data is obtained at a z-location on the z-axis. For example, slice 174 is obtained at a z-location between $z_4$ and $z_5$, slices 176 and 178 are obtained at two consecutive z-locations between $z_7$ and $z_8$, and slice 180 is obtained at a z-location between $z_9$ and $z_{10}$. Set 160, set 162, set 164, slice 174, set 166, set 168, slice 176, slice 178, set 170, slice 180, and set 172 that are consecutively ordered along the z-axis are referred to as an array 182.

Computer 36 obtains sets 160, 162, 164, 166, 168, 170, and 172 and ungated slices 174, 176, 178, and 180 of image data, and filters slices 174, 176, 178, and 180 of ungated image data. A filter, such as a comb filter, is used to filter slices 174, 176, 178, and 180 of ungated image data. To filter slices 174, 176, 178, and 180 of ungated image data, computer 36 identifies midscan times that occur once within array 182. Each set 160, 162, 164, 166, 168, 170, or 172 of image data has two or more slices of image data. Moreover, all slices of image data within each set 160, 162, 164, 166, 168, 170, or 172 have the same midscan time. For example, slices of image data within set 160 have a $\text{midscan time}_a$, slices of image data within set 162 have a $\text{midscan time}_b$, slices of image data within set 164 have a $\text{midscan time}_c$, slices of image data within set 166 have a $\text{midscan time}_d$, slices of image data within set 168 have a $\text{midscan time}_e$, slices of image data within set 170 have a $\text{midscan time}_f$, and slices of image data within set 172 have a $\text{midscan time}_g$.

Comparatively, any of slices 174, 176, 178, and 180 of ungated image data have a unique midscan time that occurs once. Computer 36 identifies slices 174, 176, 178, and 180 of ungated image data from their unique midscan times and filters slices 174, 176, 178, and 180.

The filtering that is described when describing FIGS. 7 and 8 removes misregistration of artifacts caused by an acquisition at a pitch outrunning a heart rate of patient 22. The outrunning can occur when patient 22's heart rate drops significantly during a scan, invalidating a prescribed pitch. For example, when patient 22's heart rate drops significantly during the scan, table 46 moves too fast to capture all z-location images in each phase of a heart cycle with the heart rate. In FIG. 8, which includes a coronal/sagital reformatted image 181, misregistration can be seen at z-locations of slices 174, 176, 178, and 180 of ungated image data when viewing images with a multiplanar reformat rendering from a sagittal or a coronal perspective. Artifacts due to misregistration can be apparent in coronary arteries of patient 22 when viewing images with a curved reformat rendering. Gaps caused by filtering slices 174, 176, 178, and 180 of ungated image data are smoothed by interpolation such as, linear, cubic, or the higher order interpolation.

Hence, some technical effects of the herein described systems and methods are to remove banding and to remove misregistration artifacts in images. The herein described systems and methods result in a more accurate assessment of cardiac anatomy and diagnosis of patient 22 as banding artifacts are minimized, a major productivity gain versus some manual trial- and-error methods, a more accurate assessment of cardiac anatomy and diagnosis since misregistration due to slices of ungated image data is minimized. As misregistration in high pitch cardiac scans is minimized, quicker scan time and lower dose can be more fully utilized.

It is noted that the herein described systems and methods can be applied to non-supersampled data if inherent resolution along the z-axis is deemed to be adequate. It is also noted that the herein described systems and methods are described when scanning patient 22 from a superior to an inferior position. The superior position is at a lower z-location than the inferior position. As an example, head of patient 22 lies at the superior position and feet of patient 22 lie at the inferior mode. However, in an alternative embodiment, the herein described systems and methods are described when scanning patient 22 from the inferior to the superior position. In the alternative embodiment, the superior position has a higher z-location than the inferior position. In the alternative embodiment, the last slices described above would be the first slices and the first slices described above would be the last slices. set of image data. For example, slice 108 of image data in set 94 would be the first slice and slice 106 of image data in the set would be the last slice. Moreover, it is noted that the Moreover, it is noted that the systems and methods for filtering images can be implemented in other imaging modalities such as, for instance, electron-beam tomography (EBT), positron emission tomography (PET), single photon emission computed tomography (SPECT), ultrasound imaging systems, and magnetic resonance imaging (MRI) systems. Furthermore, it is noted that the herein described systems and methods are not limited to a specific platform. For instance, the systems and methods can be implemented in an Advantage™ Windows™ workstation or in a scanner console. Additionally, although the herein described methods are described in a medical setting, it is contemplated that the benefits of the methods accrue to non-medical imaging systems such as those systems typically employed in an industrial setting or a transportation setting, such as, for example, but not limited to, a baggage scanning system for an airport, other transportation centers, government buildings, office buildings, and the like. The benefits also accrue to micro PET and CT systems which are sized to study lab animals as opposed to humans.

While the invention has been described in terms of various specific embodiments, those skilled in the art will recognize that the invention can be practiced with modification within the spirit and scope of the claims.

What is claimed is:

1. A method for filtering images, the method comprising:
    obtaining at least one set of image data of a subject using an imaging system;
    removing at least one slice of image data from the at least one set to form a filtered set; and
    reconstructing images from the filtered set.

2. A method in accordance with claim 1 wherein removing at least one slice of image data from the at least one set comprises using a filter to remove the at least one slice of image data from the at least one set.

3. A method in accordance with claim 1 wherein removing at least one slice of image data from the at least one set comprises using a comb filter to remove the at least one slice of image data from the at least one set.

4. A method in accordance with claim 1 wherein removing at least one slice of image data from the at least one set comprises removing a slice of image data located at one of a lowest z-location and a highest z-location of all z-locations in the at least one set.

5. A method in accordance with claim 1 wherein removing at least one slice of image data from the at least one set comprises removing a slice of image data located at a lowest z-location of all z-locations in the at least one set and removing a slice of image data at a highest z-location of all z-locations in the at least one set.

6. A method in accordance with claim 1 wherein obtaining at least one set of image data of a subject comprises obtaining at least one set of image data of a subject, wherein each slice of image data in the at least one set is obtained at a different z-location than z-locations of any other slices of image data in the at least one set.

7. A method in accordance with claim 1 further comprising:
    determining at least one point that lies on a z-axis along which the subject lies and at which there is a change in a midscan time, the change in the midscan time occurring between two consecutive sets of the at least one set, the two consecutive sets including a first set and a second set; and
    determining to remove at least one of a slice of image data having a highest z-location among all z-locations in the first set and a slice of image data having a lowest z-location among all z-locations in the second set.

8. A method in accordance with claim 1 further comprising:
    determining at least one point that lies on a z-axis along which the subject lies and at which there is a change in a midscan time, the change in the midscan time occurring between a set of image data of the at least one set and a slice of ungated image data; and
    determining to remove the slice of ungated image data.

9. A method for filtering images comprising:
    obtaining at least one set of image data over a range of z-locations after scanning a subject, wherein each set is acquired at the same time in a physiological cycle of motion of an object within the subject; and removing at least one slice of image data from the at least one set.

10. A computer-readable medium encoded with a program configured to:
obtain at least one set of image data of a subject using an imaging system;
remove at least one slice of image data from the at least one set to form a filtered set; and
reconstruct images from the filtered set.

11. A computer-readable medium in accordance with claim 10 wherein the program is configured to use a filter to remove the at least one slice of image data from the at least one set.

12. A computer-readable medium in accordance with claim 11 wherein the program is configured to use a comb filter to remove the at least one slice of image data from the at least one set.

13. A computer-readable medium in accordance with claim 10 wherein to remove at least one slice of image data from the at least one set the program is configured to remove a slice of image data located at one of a lowest z-location and a highest z-location of all z-locations in the at least one set.

14. A computer-readable medium in accordance with claim 10 wherein to remove at least one slice of image data from the at least one set the program is configured to remove a slice of image data located at a lowest z-location of all z-locations in the at least one set and to remove a slice of image data at a highest z-location of all z-locations in the at least one set.

15. A computer-readable medium in accordance with claim 10 wherein to obtain at least one set of image data of a subject the program is configured to obtain at least one set of image data of a subject, wherein each slice of image data in the at least one set is obtained at a different z-location than z-locations of any other slices of image data in the at least one set.

16. A computer-readable medium in accordance with claim 10 wherein the program is configured to:
determine at least one point that lies on a z-axis along which the subject lies and at which there is a change in a midscan time, the change in the midscan time occurring between two consecutive sets of the at least one set, the two consecutive sets including a first set and a second set; and
determine to remove at least one of a slice of image data having a highest z-location among all z-locations in the first set and a slice of image data having a lowest z-location among all z-locations in the second set.

17. A computer-readable medium in accordance with claim 10 wherein the program is configured to:
determine at least one point that lies on a z-axis along which the subject lies and at which there is a change in a midscan time, the change in the midscan time occurring between a set of image data of the at least one set and a slice of ungated image data; and
determine to remove the slice of ungated image data.

18. A computed tomography (CT) system comprising:
an X-ray source configured to generate X-rays;
a detector configured to detect the X-rays to generate electrical signals;
a data acquisition system (DAS) for sampling the electrical signals to create projection data that is converted into at least one set of image data;
a controller configured to:
obtain the at least one set of image data of a subject using the CT system;
remove at least one slice of image data from the at least one set to form a filtered set; and
reconstruct images from the filtered set.

19. A CT system in accordance with claim 18 wherein the controller is configured to use a filter to remove the at least one slice of image data from the at least one set.

20. A CT system in accordance with claim 19 wherein the filter is a comb filter.

21. A CT system in accordance with claim 18 wherein to remove at least one slice of image data from the at least one set the controller is configured to remove a slice of image data located at a lowest z-location of all z-locations in the at least one set.

22. A CT system in accordance with claim 18 wherein to remove at least one slice of image data from the at least one set the controller is configured to remove a slice of image data located at a lowest z-location of all z-locations in the at least one set and to remove a slice of image data at a highest z-location of all z-locations in the at least one set.

23. A CT system in accordance with claim 18 wherein to obtain at least one set of image data of a subject the controller is configured to obtain at least one set of image data of a subject, wherein each slice of image data in the at least one set is obtained at a different z-location than z-locations of any other slices of image data in the at least one set.

24. A CT system in accordance with claim 18 wherein the controller is configured to:
determine at least one point that lies on a z-axis along which the subject lies and at which there is a change in a midscan time, the change in the midscan time occurring between two consecutive sets of the at least one set, the two consecutive sets including a first set and a second set; and
determine to remove at least one of a slice of image data having a highest z-location among all z-locations in the first set and a slice of image data having a lowest z-location among all z-locations in the second set.

25. A computer configured to:
obtain at least one set of image data of a subject using an imaging system;
remove at least one slice of image data from the at least one set to form a filtered set; and
reconstruct images from the filtered set.

* * * * *